US010728434B2

(12) United States Patent
Dillon et al.

(10) Patent No.: US 10,728,434 B2
(45) Date of Patent: *Jul. 28, 2020

(54) OPTICAL COHERENCE TOMOGRAPHY IMAGING SYSTEM

(71) Applicants: Dental Imaging Technologies Corporation, Hatfield, PA (US); Ormco Corporation, Orange, CA (US)

(72) Inventors: Robert F. Dillon, Mt. Pleasant, SC (US); Amr Medhat Elbasiony, Chelmsford, MA (US)

(73) Assignees: DENTAL IMAGING TECHNOLOGIES CORPORATION, Hatfield, PA (US); ORMCO CORPORATION, Orange, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/186,110

(22) Filed: Nov. 9, 2018

(65) Prior Publication Data

US 2019/0098186 A1    Mar. 28, 2019

Related U.S. Application Data

(63) Continuation of application No. 15/215,131, filed on Jul. 20, 2016, now Pat. No. 10,129,448.

(51) Int. Cl.
*G06K 9/00*  (2006.01)
*H04N 5/225*  (2006.01)
(Continued)

(52) U.S. Cl.
CPC ......... *H04N 5/2256* (2013.01); *A61B 5/0066* (2013.01); *A61B 5/0088* (2013.01); *A61C 9/0053* (2013.01); *H04N 2005/2255* (2013.01)

(58) Field of Classification Search
CPC ............. H04N 5/2256; H04N 13/0203; H04N 2005/2255; H04N 2201/0079; A61B 1/24;
(Continued)

(56) References Cited

U.S. PATENT DOCUMENTS 9,770,217 B2    9/2017  Sandholm et al.
10,130,259 B2 *  11/2018  Lam ................... G01N 21/4795
(Continued)

FOREIGN PATENT DOCUMENTS

CN   103040429 B   6/2015
JP   2008194108 A   8/2008
(Continued)

OTHER PUBLICATIONS

Canjau, S. et al., "Optical Coherence Tomography for Non-Invasive ex vivo Investigations in Dental Medicine—a Joint Group Experience (Review)," Sovremennye tehnologii v medicine 2015; 7(1): 97-114 (Oct. 2015).
(Continued)

*Primary Examiner* — Jose L Couso
(74) *Attorney, Agent, or Firm* — Michael Best & Friedrich LLP

(57) ABSTRACT

An imaging system, a method for imaging an object of interest, and an image of the object of interest. In one embodiment, an imaging system includes a channel configured to receive information from an object of interest, a 3DSS sub-system configured to capture information from the object of interest and generate at least one of 3D surface data or 3D position data based on the information captured by the 3DSS sub-system, and an OCT sub-system configured to perform a line scan of light reflected from the object of interest, generate OCT image data from the line scan, receive the at least one of the 3D surface data or the 3D position data, and generate one or more OCT images using
(Continued)

the OCT image data and the at least one of the 3D surface data or the 3D position data.

20 Claims, 5 Drawing Sheets

(51) Int. Cl.
*A61B 5/00* (2006.01)
*A61C 9/00* (2006.01)

(58) Field of Classification Search
CPC ..... A61B 1/00009; A61B 1/0002; A61B 1/00; A61B 1/05; A61B 1/00096; A61B 1/000172; A61B 1/041; A61B 1/0661–0676; A61B 5/0066; A61B 5/0088; A61B 5/0084; A61C 9/0053; G06K 9/00; G06K 2017/009; G06K 2209/05; G06T 7/0012; G06T 2007/10068; G06T 2207/30004; G06T 2207/30036; G06T 2210/41; G01B 9/02091; G01B 9/02; G01B 2290/65; G02B 23/2423; G02B 23/2461; G02B 26/0816

See application file for complete search history.

(56) References Cited

U.S. PATENT DOCUMENTS

| | | |
|---|---|---|
| 2004/0122306 A1 | 6/2004 | Spoonhower et al. |
| 2008/0062429 A1 | 3/2008 | Liang et al. |
| 2009/0227875 A1 | 9/2009 | Cao et al. |
| 2010/0290059 A1 | 11/2010 | Inoue |
| 2012/0238882 A1 | 9/2012 | Chou et al. |
| 2013/0183633 A1 | 7/2013 | Dillon et al. |
| 2013/0330686 A1 | 12/2013 | Kaji et al. |
| 2014/0146142 A1 | 5/2014 | Duret et al. |
| 2014/0272764 A1 | 9/2014 | Miller et al. |
| 2014/0309527 A1 | 10/2014 | Namati et al. |
| 2014/0342301 A1 | 11/2014 | Fleer et al. |
| 2016/0256051 A9 | 9/2016 | Kulkarni |
| 2016/0338803 A1 | 11/2016 | Pesach |
| 2017/0119505 A1 | 5/2017 | Mormann et al. |
| 2017/0215997 A1 | 8/2017 | Martin |
| 2017/0248412 A1 | 8/2017 | Lampert et al. |
| 2018/0085002 A1 | 3/2018 | Glinec et al. |
| 2018/0296080 A1* | 10/2018 | Glinec ............... G06T 1/0007 |
| 2018/0357766 A1* | 12/2018 | Van Der Poel ........ A61B 6/145 |
| 2019/0117075 A1* | 4/2019 | Fan ...................... A61B 5/0066 |
| 2019/0117076 A1* | 4/2019 | Fan ...................... G06T 11/006 |
| 2019/0117078 A1* | 4/2019 | Sharma .................... A61B 1/24 |
| 2019/0133725 A1* | 5/2019 | Wong ...................... G06T 7/50 |
| 2019/0328489 A1* | 10/2019 | Capron-Richard ......................... G06T 7/0012 |

FOREIGN PATENT DOCUMENTS

| | | |
|---|---|---|
| WO | 2008063605 | 5/2008 |
| WO | 2016002432 | 1/2016 |

OTHER PUBLICATIONS

Nkenke, E. et al., "Fusion of computed tomography data and optical 30 images of the dentition for streak artefact correction in the simulation of orthognathic surgery", Dentomaxillofacial Radiology (2004) vol. 33, pp. 226-232.

International Search Report and Written Opinion for Application No. PCT/US2017/039569 dated Oct. 3, 2017 (17 pages).

European Patent Office Extended Search Report for Application No. 17831540.4 dated Jan. 23, 2020 (7 pages).

Japanese Patent Office Action for Application No. 2019-502177 dated Feb. 13, 2020 (11 pages, English translation included).

\* cited by examiner

OPTICAL COHERENCE TOMOGRAPHY IMAGING SYSTEM

CROSS-REFERENCE TO RELATED APPLICATION

This application is a continuation of U.S. application Ser. No. 15/215,131, filed on Jul. 20, 2016, the entire content of which is hereby incorporated by reference.

FIELD

The disclosure relates to optical coherence tomography.

BACKGROUND

Optical coherence tomography is an imaging technique that uses light to capture volumetric three-dimensional images of objects. The images may include both surface and sub-surface features. Optical coherence tomography may use near-infrared light and may be based on low-coherence interferometry.

A three-dimensional (3D) intra-oral image system measures topographical characteristics of teeth and soft tissue surfaces. The 3D intra-oral image system may include an intra-oral camera with a light source. The 3D intra-oral image system may be inserted into the mouth of a patient. After insertion, the 3D intra-oral image system captures images of visible parts of the patient's teeth and surrounding tissue. The 3D intra-oral image system may generate a model of the patient's teeth that may be used in place of traditional cast impressions.

SUMMARY

One embodiment provides an imaging system that includes a channel, a three-dimensional surface scanning (3DSS) sub-system, and an optical coherence tomography (OCT) sub-system. The channel is configured to receive information from an object of interest. The three-dimensional surface scanning (3DSS) sub-system is configured to capture information from the object of interest and generate at least one of three-dimensional surface data or three-dimensional position data based on the information captured by the 3DSS sub-system. The optical coherence tomography (OCT) sub-system is configured to perform a line scan of light reflected from the object of interest and captured by the OCT sub-system, generate optical coherence tomography (OCT) image data from the line scan. The optical coherence tomography (OCT) sub-system is also configured to receive the at least one of the three-dimensional surface data or the three-dimensional position data from the 3DSS sub-system, and generate one or more optical coherence tomography (OCT) images using the OCT image data and the at least one of the three-dimensional surface data or the three-dimensional position data. Each of the three-dimensional surface data and the three-dimensional position data is indicative of a common spatial frame of reference between the 3DSS sub-system and the OCT sub-system.

Another embodiment provides a method of imaging an object of interest. The method includes capturing, with a three-dimensional surface scanning (3DSS) sub-system, information from an object of interest. The method includes generating, with the 3DSS sub-system, at least one of three-dimensional surface data or three-dimensional position data based on the information captured by the 3DSS sub-system. The method includes performing, with the OCT sub-system, a line scan of light captured by the OCT sub-system to generate OCT image data. The method includes receiving, with the OCT sub-system, the at least one of the three-dimensional surface data or the three-dimensional position data from the 3DSS sub-system. Additionally, the method includes generating, with the OCT sub-system, one or more optical coherence tomography (OCT) images based on the OCT image data and the at least one of the three-dimensional surface data or the three-dimensional position data.

Yet another embodiment provides a three-dimensional surface scan and optical coherence tomography (3DSS/OCT) image including a first image portion based on a surface of an object of interest and a second image portion based at least in part on a sub-surface of the object of interest.

Other aspects and embodiments will become apparent by consideration of the detailed description and accompanying drawings.

BRIEF DESCRIPTION OF THE DRAWINGS

The accompanying figures, where like reference numerals refer to identical or functionally similar elements throughout the separate view, together with the detailed description below, are incorporated in and form part of the specification, and serve to further illustrate embodiments of concepts that include the claimed invention, and explain various principles and advantages of those embodiments.

Figure 1:
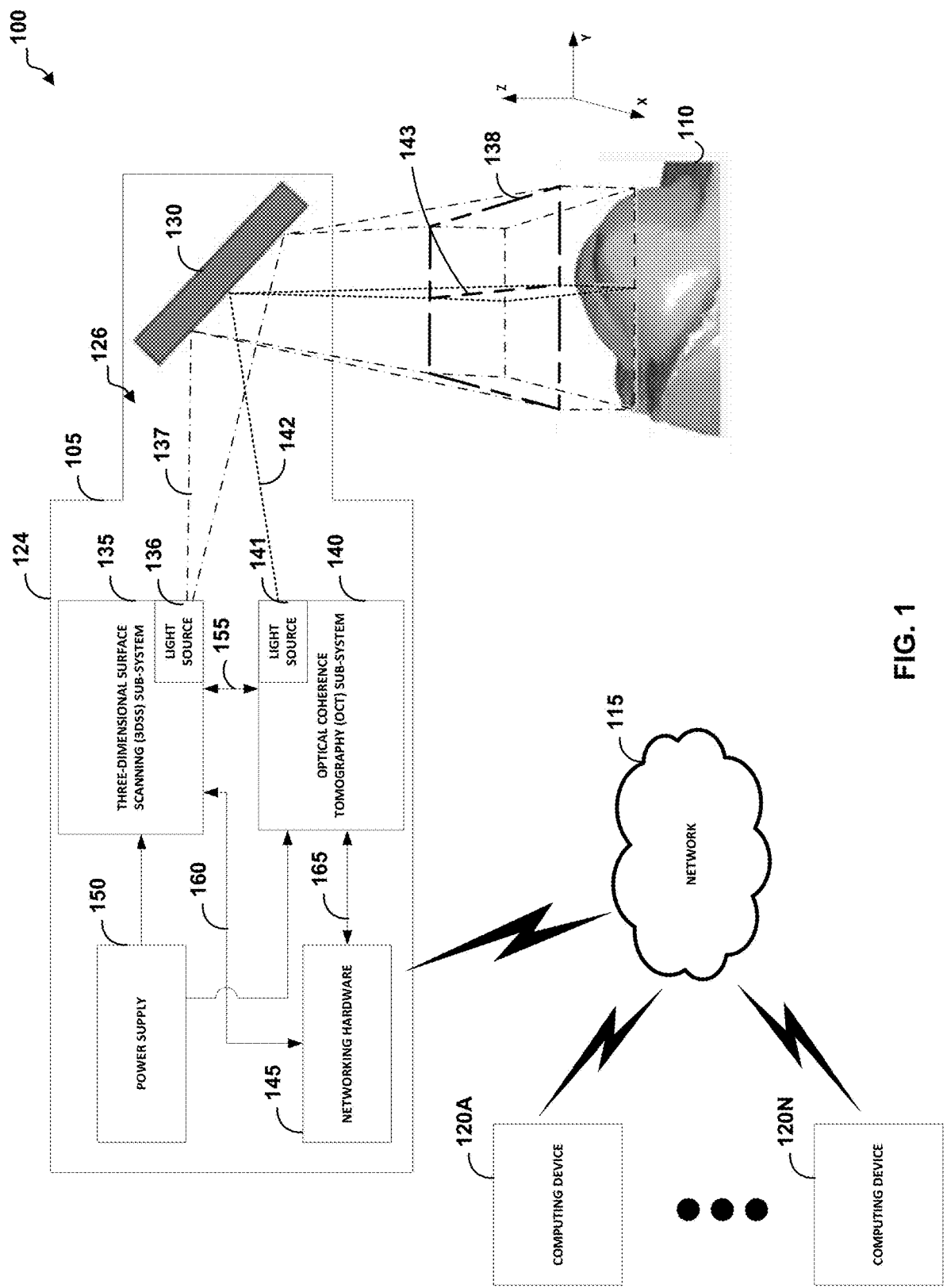
FIG. 1 is a diagram of an imaging environment that includes an imaging system in accordance with some embodiments.

Skilled artisans will appreciate that elements in the figures are illustrated for simplicity and clarity and have not necessarily been drawn to scale. For example, the dimension of some of the elements in the figures may be exaggerated relative to other elements to help improve understanding of embodiments of the present invention.

The apparatus and method components have been represented where appropriate by conventional symbols in the drawings, showing only those specific details that are pertinent to understanding the embodiments of the present invention so as not to obscure the disclosure with description herein.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways, and in various applications, including dental imaging applications among other imaging applications.

A conventional optical coherence tomography system has a line scan axis and a second scan axis perpendicular to the line scan axis to create a two-dimensional (2D) raster scan of an object. However, due to the relative motion of the conventional optical coherence tomography system during in-vivo applications (for example, hand-held scans of a patient's mouth), line-to-line positioning errors distort the in-vivo objects of interest in the raster image. Additionally, the conventional optical coherence tomography system requires two optical channels, an optical coherence tomography measurement channel that provides the line scan axis and a reference channel that provides controlled optical radiation that, when combined with light from measurement channel, generates coherent optical interference from both surface and sub-surface object features.

To help reduce the line-to-line positioning errors, some embodiments of imaging systems described herein include a three-dimensional surface scanning sub-system (referred to herein as "3DSS sub-system") that performs a surface scan of the object of interest and an optical coherence tomography sub-system (referred to herein as "OCT sub-system") that performs a line scan with a single axis of the object of interest. Both the 3DSS sub-system and the OCT sub-system share the same spatial frame of reference. The line scan of the OCT sub-system may be stitched together in proper orientation using surface data, position data, or a combination thereof generated by the 3DSS sub-system in real time and in synchrony with the line scan performed by the OCT sub-system.

FIG. 1 is a diagram of an imaging environment 100 including an imaging system 105, in accordance with some embodiments. In the illustrated embodiment, the imaging environment 100 is described with respect to an intra-oral dental imaging environment. However, in other embodiments, the imaging environment 100 may be described with respect to other imaging environments associated with other imaging applications. In the example illustrated, the imaging environment 100 includes an imaging system 105. The imaging system 105 is used to capture information or data from an object or tissue of interest 110, for example, dentition and surrounding tissue within the intra-oral dental imaging environment. In the example of FIG. 1, the imaging environment 100 also includes a network 115, and one or more computing devices 120A-120N (collectively "computing devices 120"). The imaging system 105 may also include additional or different components than those components illustrated in FIG. 1 and may be configured to perform additional functionality or different functionality than the functionality described herein.

The imaging system 105 includes a housing 124, an optical channel 126, a mirror 130, an 3DSS sub-system 135, an OCT sub-system 140, networking hardware 145, and a power supply 150. The housing 124 partially encloses the mirror 130 at one end of the housing 124. The housing 124 also encloses the 3DSS sub-system 135, the OCT sub-system 140, the networking hardware 145, and the power supply 150. In some embodiments, the housing 124 is a handheld device. In some embodiments, the power supply 150 is a rechargeable battery that provides power to at least the 3DSS sub-system 135 and the OCT sub-system 140 as indicated by one-sided arrows. In some embodiments, the 3DSS sub-system may be a three-dimensional intra-oral digital impression sub-system (referred to as a "DIS") that measures a three-dimensional volume and performs a three-dimensional surface scan of the object of interest. For example, the three-dimensional intra-oral digital impression sub-system may be a Lythos system from Ormco Corporation. For ease of understanding, the 3DSS sub-system 135 is described herein with the structure and functionality of a digital impression system (DIS) that captures information of an object of interest from light. However, in other embodiments, the 3DSS sub-system 135 may be a surface scanning sub-system that captures information of an object of interest from other mediums, in place of or in addition to light. In addition, the 3DSS sub-system 135 is not limited to the structure and functionality of the DIS. For example, in other embodiments, the 3DSS sub-system 135 may include one or more ultrasonic transducers, one or more acoustic receivers, or other devices for capturing information of the object of interest, in place of or in addition to, the DIS as described below.

In the example illustrated, the 3DSS sub-system 135 includes a light source 136 that emits light 137. The light 137 is reflected off of the mirror 130 and illuminates the object of interest 110. When the light 137 illuminates the object of interest 110, a portion of the light 137 is reflected back to the mirror 130, and this portion of the light 137 is indicative of a three-dimensional measurement volume 138 (referred to as "the light indicative of the three-dimensional measurement volume 138").

In the example illustrated, the OCT sub-system 140 includes a light source 141 that emits light 142. The light 142 is reflected off of the mirror 130 and illuminates the object of interest 110. When the light 142 illuminates the object of interest 110, a portion of the light 142 is reflected back to the mirror 130, and this portion of the light 142 is indicative of an optical coherence tomography (OCT) line measurement 143 (referred to as "the light indicative of the OCT line measurement 143").

The 3DSS sub-system 135 receives and processes the light indicative of the three-dimensional measurement volume 138. Similarly, the OCT sub-system 140 receives and processes the light indicative of the OCT line measurement 143. In some embodiments, the mirror 130 redirects the light indicative of the three-dimensional measurement volume 138 and the light indicative of the OCT line measurement 143 to the 3DSS sub-system 135 and the OCT sub-system 140, respectively.

In the illustrated embodiments, the 3DSS sub-system 135 is disposed in the housing 124 to emit the light 137 and receive the light indicative of the three-dimensional measurement volume 138. In other embodiments, the 3DSS sub-system could be located outside the housing 124. The 3DSS sub-system 135 performs a three-dimensional area scan using the light indicative of the three-dimensional measurement volume 138 to generate three-dimensional surface data, three-dimensional position data, a combination thereof, and/or three-dimensional surface scanning (3DSS) image data.

Figure 2:
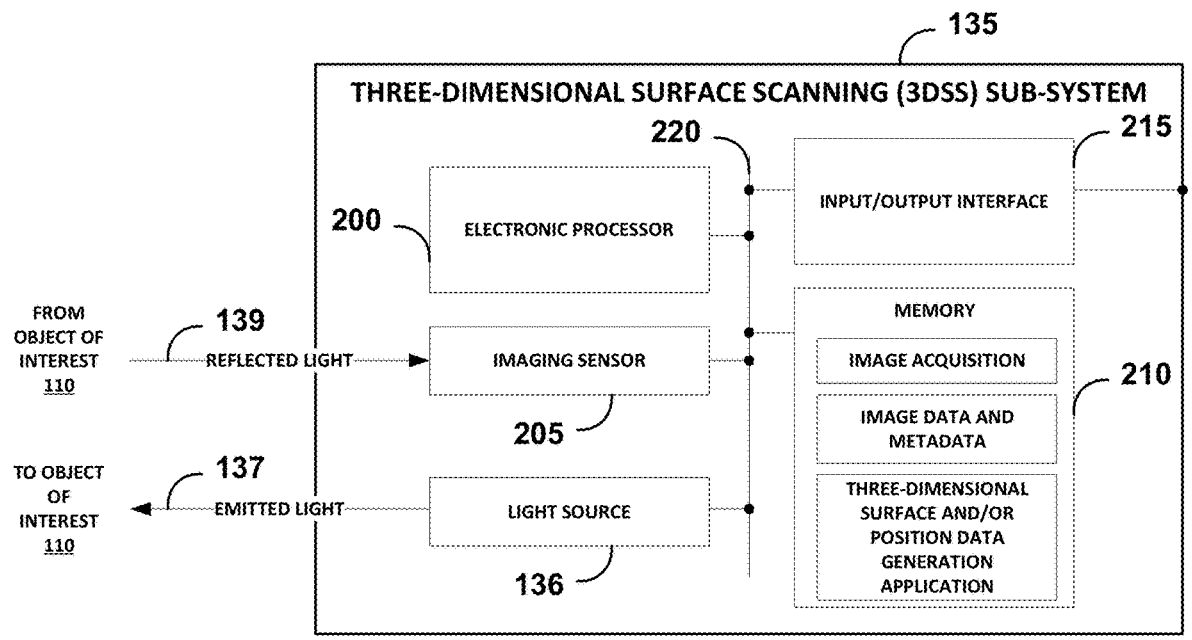
FIG. 2 is a block diagram of a three-dimensional surface scanning (3DSS) sub-system of the imaging system of FIG. 1, in accordance with some embodiments.

For example, FIG. 2 is a block diagram of the 3DSS sub-system 135 of the imaging system 105 of FIG. 1, in accordance with some embodiments. The 3DSS sub-system 135 includes the light source 136, an electronic processor 200, an imaging sensor 205 (for example, a three-dimensional surface scanning imaging sensor), a memory 210, an input/output interface 215, and a communication bus 220. The light source 136, the electronic processor 200, the imaging sensor 205, the memory 210 (a non-transitory computer-readable medium), the input/output interface 215 are electrically and communicatively connected to each other over the communication bus 220 or other suitable connections. Software stored on the memory 210 may include instructions that when executed, cause the electronic processor 200 to perform some or all of the methods described herein. The 3DSS sub-system 135 may also include additional or different components than those components illustrated in FIG. 2 and may be configured to perform additional functionality than the functionality described herein.

For example, the electronic processor 200 controls the light source 136 to emit the light 137 to illuminate the object of interest 110. The electronic processor controls the imaging sensor 205 to capture reflected light 139 that is indicative of the three-dimensional measurement volume 138. The electronic processor 200 executes three-dimensional surface and/or position data generation application stored in the memory 210 to generate the three-dimensional surface data, the three-dimensional position data, or a combination thereof from the three-dimensional area scan of the object of interest 110 using the reflected light 139. In some embodiments, the electronic processor 200 may store the three-dimensional surface data, the three-dimensional position data, or the combination thereof as metadata in the memory 210. In other embodiments, the electronic processor 200 may control the input/output interface 215 to communicate the three-dimensional surface data, the three-dimensional position data, or the combination thereof with systems and devices external to the 3DSS sub-system 135. For example, the input/output interface 215 can communicate with the OCT sub-system 140 over a connection 155 or the networking hardware 145 over a connection 160 including a wire or a cable. In other embodiments, the connections 155 and 160 may be wireless connections.

Referring back to the illustrated embodiment of FIG. 1, the OCT sub-system 140 may also be disposed in the housing 124 to emit the light 142 with a single axis and receive the light indicative of the OCT line measurement 143. The OCT sub-system 140 performs a line scan using the light indicative of the OCT line measurement 143 to generate optical coherence tomography (OCT) image data that has only a single scan axis.

Figure 3:
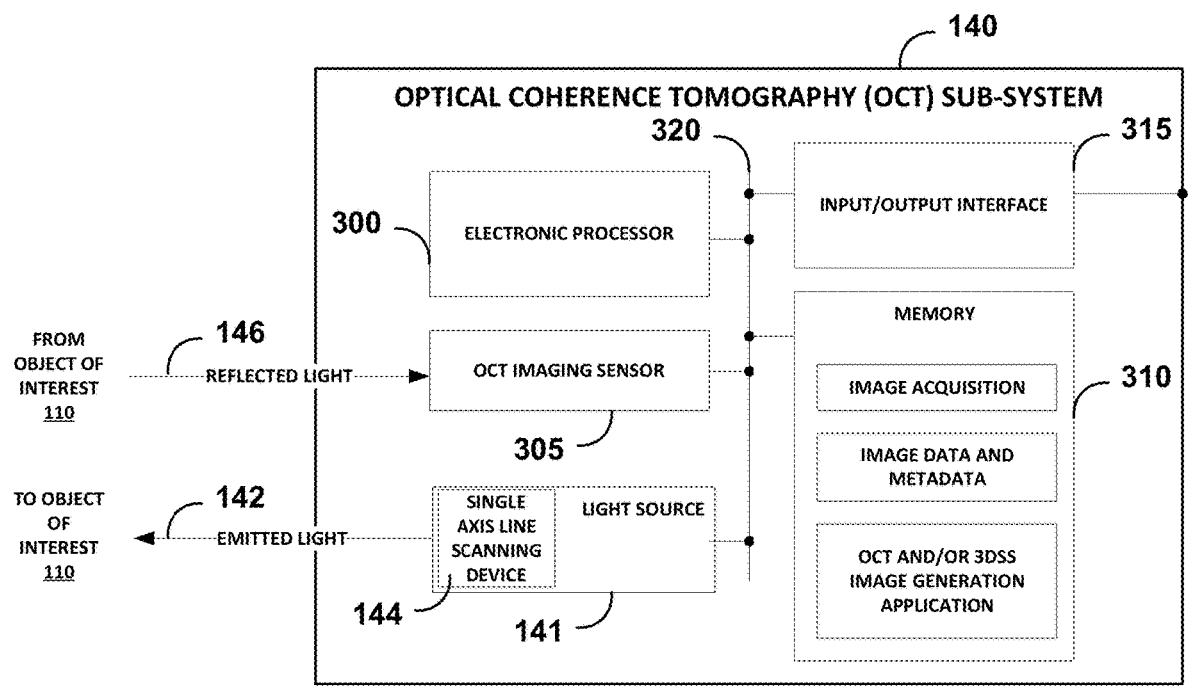
FIG. 3 is a block diagram of an optical coherence tomography (OCT) sub-system of the imaging system of FIG. 1, in accordance with some embodiments.

For example, FIG. 3 is a block diagram of the OCT sub-system 140 of the imaging system 105 of FIG. 1, in accordance with some embodiments. The OCT sub-system 140 includes, the light source 141, an electronic processor 300, an optical coherence tomography (OCT) imaging sensor 305, a memory 310, an input/output interface 315, and a communication bus 320. The light source 141 also includes single axis line scanning device 144. The light source 141, the electronic processor 300, the OCT imaging sensor 305, the memory 310 (for example, a non-transitory computer-readable medium), the input/output interface 315 are electrically and communicatively connected to each other over the communication bus 320 or other suitable components. Software stored on the memory 310 may include instructions that when executed, cause the electronic processor 300 to perform some or all of the methods described herein. The OCT sub-system 140 may include additional or different components than those components illustrated in FIG. 3 and may be configured to perform additional functionality than the functionality described herein.

In illustrated embodiment of FIG. 3, the electronic processor 300 controls the single axis line scanning device 144 to emit the light 142 with a single axis that illuminates the object of interest 110. The electronic processor 300 controls the OCT imaging sensor 305 to capture reflected light 146 that is indicative of the OCT line measurement 143. The electronic processor 300 executes an OCT and/or 3DSS generation application stored in the memory 310 to perform the methods described herein.

The input/output interface 315 communicates with systems and devices external to the OCT sub-system 140. For example, the input/output interface 315 can communicate with the 3DSS sub-system 135 over the connection 155 or the networking hardware 145 over a connection 165 including a wire or a cable. In other embodiments, the connection 165 may be a wireless connection.

In some embodiments, the electronic processors 200 and 300 are each a microprocessor or an application-specific integrated circuit ("ASIC"), or other suitable processing device. In some embodiments, the imaging sensor 205 and the OCT imaging sensor 305 are each a semiconductor charge-coupled device (CCD), a complementary metal-oxide-semiconductor (CMOS), N-type metal-oxide-semiconductor (NMOS), or other suitable imaging sensor. In some embodiments, the memory 210 and 310 are each a non-transitory computer-readable medium including random access memory ("RAM"), read-only memory ("ROM"), or other suitable non-transitory computer-readable medium.

Referring back to FIG. 1, in the illustrated embodiment, the 3DSS sub-system 135 and/or the OCT sub-system 140 are electrically connected to the networking hardware 145 with the connections 160 and 165. The networking hardware 145 receives image data, images, and/or metadata. The networking hardware 145 transmits the image data, images, and/or the metadata, to at least one of the computing devices 120 via the network 115. In some embodiments, the at least one of the computing devices 120 includes a display, which may display the images. In other embodiments, the computing devices 120 may use an electronic processor to process the image data and metadata to generate images, and control a display to display the images.

The image data may include the 3DSS image data or the OCT image data as described above. The images may include at least one of one or more 3DSS images, one or more OCT images, or one or more 3DSS/OCT images as described in greater detail below. The metadata may include the three-dimensional surface data, the three-dimensional position data, or a combination thereof. In some embodiments, the networking hardware 145 includes a Wi-Fi transceiver, a cellular network transceiver, a BLUETOOTH transceiver, an Ethernet modem, or other suitable networking hardware. In some embodiments, the network 115 may include a local area network, an intranet, the Internet, a storage area network, BLUETOOTH area network, cellular network, or other suitable network. In some embodiments, the computing devices 120 may include a personal computer, a server, a smartphone, a mobile computation device, a dental workstation, a tablet computing device, or other suitable computing device. For ease of understanding, the imaging system 105 has been described as including the mirror 130. However, in some embodiments, the imaging system 105 may not include the mirror 130. For example, instead of using the mirror 130, the 3DSS sub-system 135 and the OCT sub-system 140 of the imaging system 105 may directly illuminate the object of interest 110.

An imaging system 105 that includes the 3DSS sub-system 135 and the OCT sub-system 140 may provide certain benefits. One benefit of the imaging system 105 is the ability to measure sub-surface three-dimensional (3D) volumetric features without the use of x-rays. Another benefit of the imaging system 105 is a higher spatial resolution of sub-surface 3D volumetric features that are captured by imaging system 105 when compared to a spatial resolution of the sub-surface 3D volumetric features captured using x-rays. Another benefit of the imaging system 105 is the use of the OCT sub-system 140 in an in vivo, hand held instrumentation. Yet another benefit of the imaging system 105 is the ability to use the 3DSS image data (for example, surface scan image data) obtained by the 3DSS sub-system 135 and the OCT image data (for example, surface and/or sub-surface scan data) obtained by the OCT sub-system 140 in combination to generate an image (for example, a 3DSS image, an OCT image, or a 3DSS/OCT image) with less noise and artifacts than conventional 3DSS images or conventional OCT images.

Figure 4:
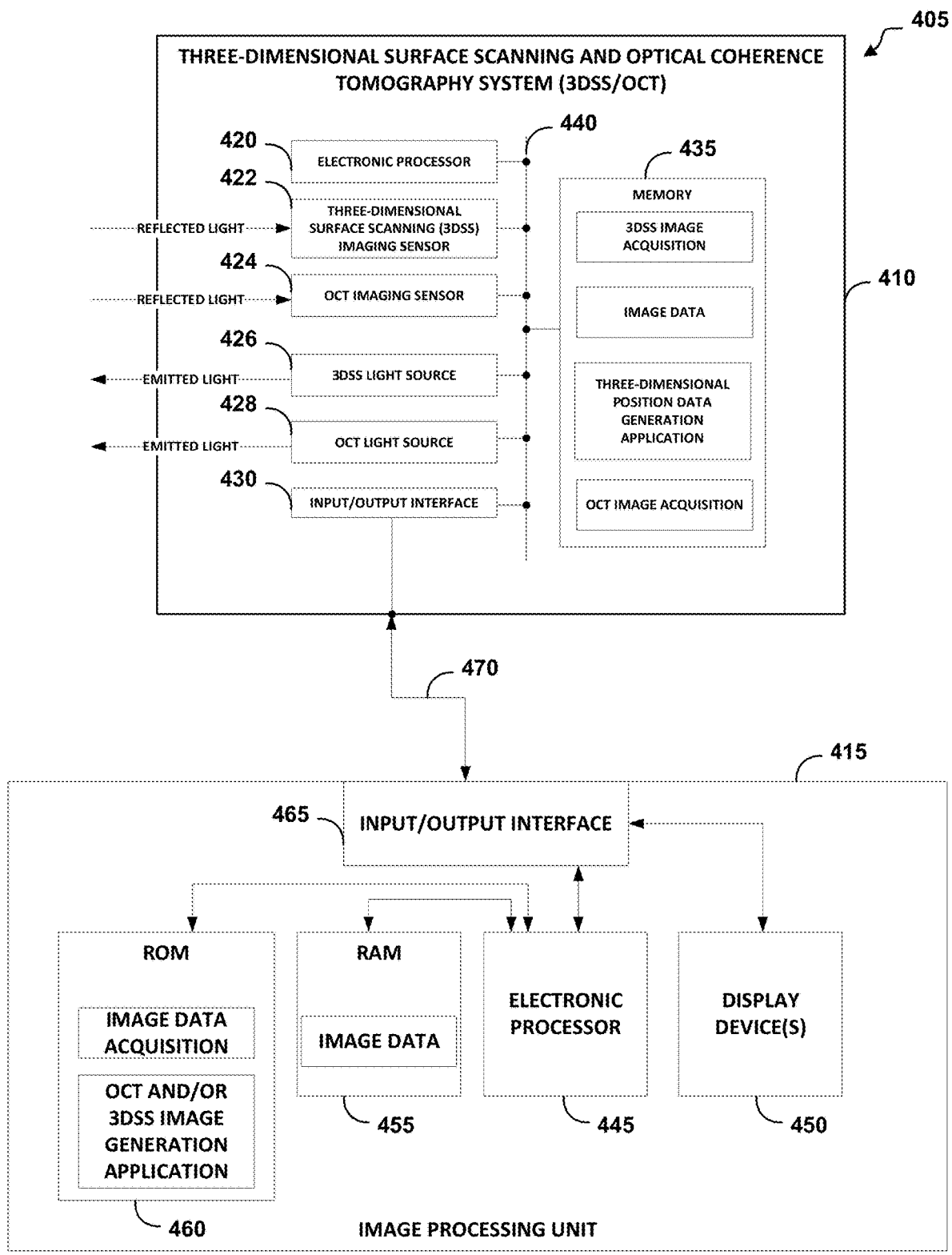
FIG. 4 is a block diagram of another imaging system, in accordance with some embodiments.

FIG. 4 is a block diagram of another imaging system 405, in accordance with some embodiments. The imaging system 405 includes a three-dimensional surface scanning and optical coherence tomography system 410 (referred to as "3DSS/OCT 410") and an image processing unit 415. The 3DSS/OCT 410 includes an electronic processor 420, a three-dimensional surface scanning imaging sensor 422, an optical coherence tomography (OCT) imaging sensor 424, a three-dimensional surface scanning (3DSS) light source 426, an optical coherence tomography (OCT) light source 428, an input/output interface 430, a memory 435, and a communication bus 440. The image processing unit 415 includes an electronic processor 445, a display device 450, random access memory 455, read-only memory (ROM) 460, and input/output interface 465.

The 3DSS/OCT 410 includes a combination of components that is similar to the combination of components included in the 3DSS sub-system 135 and the OCT sub-system 140 as described above. As a consequence, this combination of components will not be described in greater detail.

The image processing unit 415 may be part of a handheld housing or part of a standalone housing (for example, a dental workstation or tablet). In the example of FIG. 4, the 3DSS/OCT 410 is communicatively connected to the image processing unit 415 using the connection 470 (for example, a wire, cable, or other suitable electrical connection) between the input/output interface 465 of the image processing unit 415 and the input/output interface 430 of the 3DSS/OCT 410. In other embodiments, the connection 470 between the image processing unit 415 and 3DSS/OCT 410 includes a wireless connection (for example, a BLUETOOTH connection, a Wi-Fi connection, or other suitable wireless connection).

The image processing unit 415 and the 3DSS/OCT 410 are collectively referred to herein as the imaging system 405. In some embodiments, the electronic processor 445 (for example, a microprocessor or an application-specific integrated circuit ("ASIC")) monitors and controls the operation of the 3DSS/OCT 410. The image processing unit 415 also includes a non-transitory computer-readable medium, for example, a random access memory ("RAM") module 455 and a read-only memory ("ROM") module 460. The software stored on the ROM module 460 may include instructions, that when executed, cause the electronic processor 445 to perform some or all of the methods described herein. In some embodiments, the software stored on the ROM module 460 is the Lythos digital impression system software provided by Ormco Corporation.

In addition, the image processing unit 415 includes an input/output interface 465. The input/output interface 465, in addition to communicating with the 3DSS/OCT 410 over the connection 470, communicates with systems and devices external to the image processing unit 415 (for example, an external display, or other suitable input and output devices).

In some embodiments, the input/output interface 465 communicates with one or more external data storage devices that may store images generated by the image processing unit 415, which can include cloud storage. As also illustrated in FIG. 4, the input/output interface 465 may also communicate with at least the display device 450. The display device 450 may be used to display images generated or received by the image processing unit 415. In particular, during operation of the 3DSS/OCT 410, information including three-dimensional surface scanning (3DSS) image data is captured by the three-dimensional surface scanning (3DSS) imaging sensor 422 and OCT image data is captured by the OCT imaging sensor 424. The 3DSS image data and the OCT image data may be processed by the image processing unit 415 to generate one or more images, and the one or more images may be sent to the display device 450 where the one or more images may be viewed. In some embodiments, the display device 450 includes a touchscreen that receives input from an operator. The image processing unit 415 can also include one or more additional peripheral devices for receiving input from an operator (for example, a keyboard, mouse, joystick, or other suitable user interface device).

The 3DSS/OCT 410 may be configured to carry out all or a portion of the image processing carried out by the image processing unit 415. In other words, imaging processing may be distributed between the 3DSS/OCT 410 and the image processing unit 415. For example, processing hardware may be located in the handheld housing of the 3DSS/OCT 410 or in the connection 470 connecting the 3DSS/OCT 410 to the image processing unit 415.

Figure 5:
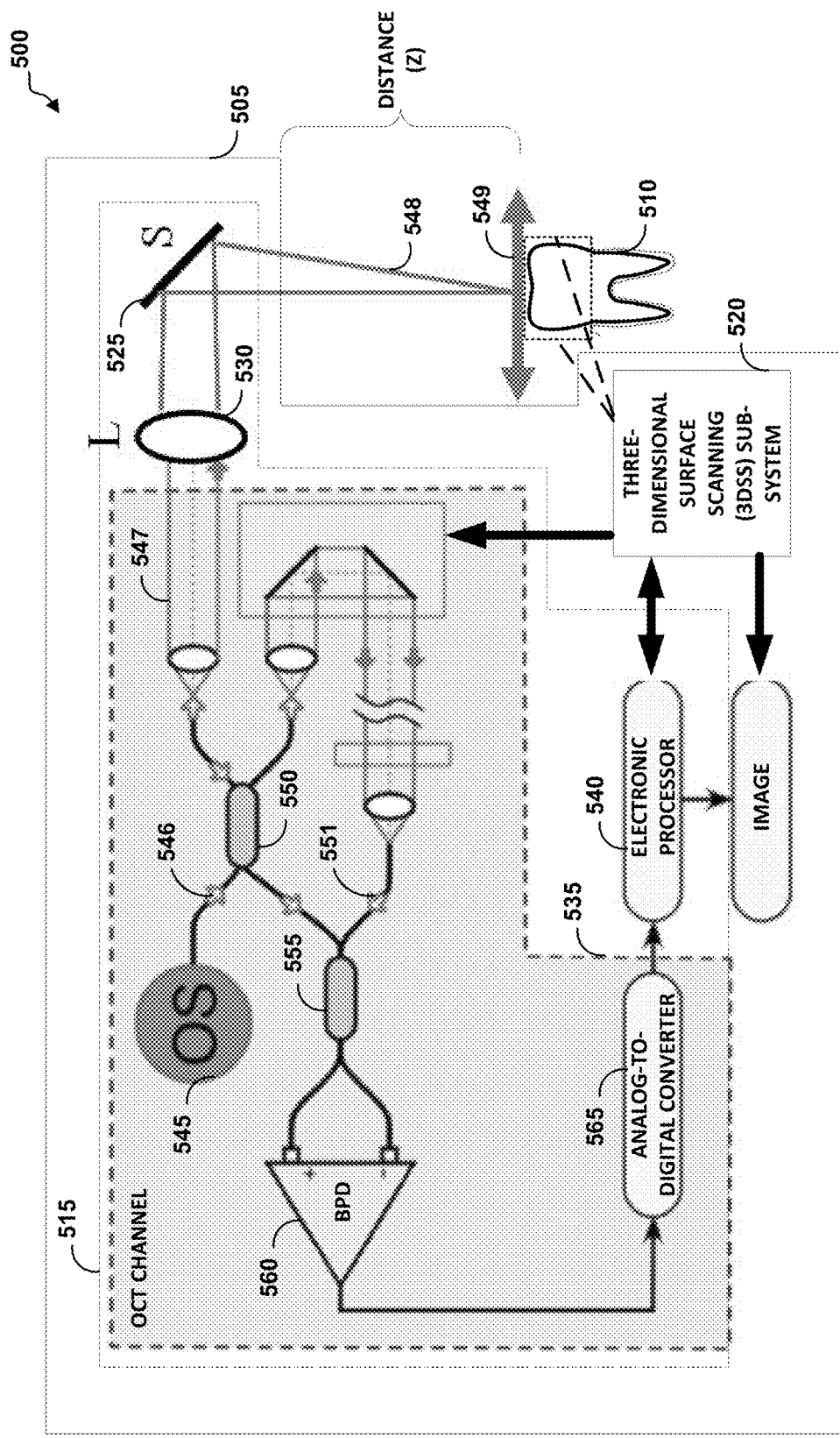
FIG. 5 is another imaging environment that includes an imaging system and one or more objects of interest, in accordance with some embodiments.

FIG. 5 is another imaging environment 500 that includes an imaging system 505 and one or more objects of interest 510, in accordance with some embodiments. The imaging system 505 includes an optical coherence tomography (OCT) sub-system 515 and a three-dimensional surface scanning (3DSS) sub-system 520. For ease of understanding, the 3DSS sub-system 520 is described herein with the structure and functionality of a digital impression system (DIS). However, in other embodiments, the 3DSS sub-system 520 may be a different surface scanning sub-system with a different structure and/or functionality than the DIS, and the 3DSS sub-system 520 is not limited to the structure and functionality of the DIS. For example, in other embodiments, the 3DSS sub-system 520 may include one or more ultrasonic transducers, one or more acoustic receivers, or other devices for capturing information of the three-dimensional surface data, the three-dimensional position data, or a combination thereof, in place of or in addition to, the DIS as described below. In some embodiments, the one or more objects of interest 510 is dentition and surrounding tissue within the imaging environment 500.

The OCT sub-system 515 includes a scanning mirror 525, a lens 530, an OCT channel 535, and an electronic processor 540. The OCT channel 535 includes a light source 545 ("OS"), a first directional coupler 550, a second directional coupler 555, a balanced photo-detector 560, and an analog-to-digital converter 565. The OCT channel 535 is one example embodiment of the OCT imaging sensor 305 and 424 as described above.

The OCT sub-system 515 has a limited distance (Z) measurement range because imaging artifacts are generated when the OCT sub-system 515 is placed too close or too far from the object of interest 510 being measured by the OCT sub-system 515. A conventional OCT system contains a reference channel. In the conventional OCT system, the length of the reference channel can be adjusted to accommodate varying object standoff distances. However, the command signal required to inform the conventional OCT system of the necessary length for the reference channel is not easily derived from the OCT channel, and instead uses a separate measurement instrument bundled in with the OCT channel to measure the object standoff, for example a confocal optical sensor system. The confocal optical sensor system measures the object standoff and does not provide information (for example, surface scan data) that may be used to provide the measure of distance (Z) and stitch together the raster scan performed by the OCT sub-system 515.

In the example of FIG. 5, the 3DSS sub-system 520 uses a light source separate from the light source 545 to perform a three-dimensional area scan of the object of interest 510 (represented by the dotted box) to generate three-dimensional surface measurement data, three-dimensional position data, or a combination thereof. The three-dimensional surface measurement data, the three-dimensional position data, or a combination thereof may be used in the imaging system 505 to reduce or eliminate errors associated with distance (Z) misplacement of the OCT sub-system 515, establish a reliable way to inform the OCT channel 535 of the reference channel length, and eliminate the additional hardware associated with the confocal measurement channel. In particular, the OCT sub-system 515 and the 3DSS sub-system 520 share a common mechanical mounting structure, and thus share a common spatial frame of reference. The common spatial frame of reference allows the 3DSS sub-system 520 to feed a signal indicative of the distance information (for example, the three-dimensional position data including the distance (Z) from the object of interest 510) directly to the OCT channel 535 and the electronic processor 540 of the OCT sub-system 515. In some embodiments, the signal indicative of the distance information that is fed from the 3DSS sub-system 520 to the OCT sub-system 515 may be calibrated at the time of manufacturing to provide a precise measurement of the distance (Z). Additionally or alternatively, in other embodiments, the signal indicative of the distance information that is fed from the 3DSS sub-system 520 to the OCT sub-system 515 may be calibrated before each distance measurement to improve precision of the measurement of the distance (Z). In some embodiments, the common mechanical mounting structure shared by the OCT sub-system 515 and the 3DSS sub-system 520 may be calibrated at the time of manufacturing to provide a precise measurement of the distance (Z) between the OCT sub-system and the object of interest 510.

In the OCT channel 535, the light source 545 emits light 546 that is injected into a first directional coupler 550. The directional coupler 550 splits the light 546 so that the light 546 is directed to two arms of the interferometer, the probing arm and the reference arm. In the example of FIG. 5, the probing beam 547 of the OCT channel 535 is adjusted by the lens 530 and reflected by the scanning mirror 525 towards the object of interest 510. The scanning mirror 525 functions as the single axis scanning device of the OCT sub-system 515 to transform the probing beam 547 of the OCT channel 535 into light 548 with a single axis. The light 548 with the single axis is scattered and a portion of the light 548 is reflected back by the object of interest 510. This portion of the light 548 is indicative of an optical coherence tomography (OCT) line measurement 549 and passes a second time through the OCT channel 535 and is guided via the first directional coupler 550 toward the second directional coupler 555, where the light indicative of the OCT line measurement 549 interferes with the light 551 coming from the reference arm of the OCT channel 535. The outputs from the second directional coupler 555 are each connected to two-pin photo-detectors in a balanced photo-detection (BPD) unit 560. The BPD unit 560 outputs the analog OCT signal to the analog-to-digital converter 565, which converts the analog OCT signal into a digital OCT signal. The electronic processor 540 stores the digital OCT signal as OCT image data in a memory. In some embodiments, the electronic processor 540 may also rectify and low-pass filter the digital OCT signal before storing the digital OCT signal.

The OCT sub-system 515 performs a line scan with a single axis in combination with the scanning mirror 525. This results in a more reliable and less expensive imaging system 505 because the confocal subsystem (including the beam combiners and second scan axis of the conventional OCT system) can be eliminated. That is, by coupling the single line scan (B-scan) modality of OCT sub-system 515 with real-time three-dimensional surface data, three-dimensional position data, or a combination thereof from the 3DSS sub-system 520 in a common spatial frame of reference, motion induced and stitching errors may be reduced or eliminated in software. Moreover, by determining the position or range of the object of interest 510 using the three-dimensional surface data, the three-dimensional position data, or a combination thereof, imaging parameters of the OCT sub-system 515 may be adjusted in real-time to capture OCT image data at the appropriate z depth, further increasing the ease of use of an OCT system including in vivo handheld applications. For example, by determining the range of the object of interest 510, the OCT sub-system may adjust in real-time the reference arm of the OCT channel 535 or the intensity of the light 546 from the light source 545 to capture OCT image data the appropriate measurement range (for example, the appropriate z depth). Additionally, the 3DSS image data and the OCT image data generated with a common spatial frame of reference may permit the interpretation or elimination of imaging artifacts inherent in the OCT image data.

An imaging system 505 that includes the OCT sub-system 515 and the 3DSS sub-system 520 may provide certain benefits. One benefit of the imaging system 505 is the elimination of the complex optical hardware required in the reference channel to perform the second axis scan of the conventional OCT system. Another benefit of the imaging system 505 is the generation of OCT images of in-vivo objects of interest with reduced or no line-to-line positioning errors by processing OCT image data from the OCT sub-system 515 with the three-dimensional surface data, the three-dimensional position data, or a combination thereof, from the 3DSS sub-system 520. Yet another benefit of the imaging system 505 is the generation of a three-dimensional surface scan and optical coherence tomography (3DSS/OCT) image that may include a fusion of the 3DSS image data (for example, surface scan image data) obtained by the 3DSS sub-system 520 and the OCT image data (for example, surface and/or sub-surface scan data) obtained by the OCT sub-system 515. The 3DSS/OCT image, when displayed on a display device, may allow a dental practitioner to view both surface and sub-surface aspects of the object of interest 510.

Figure 6:
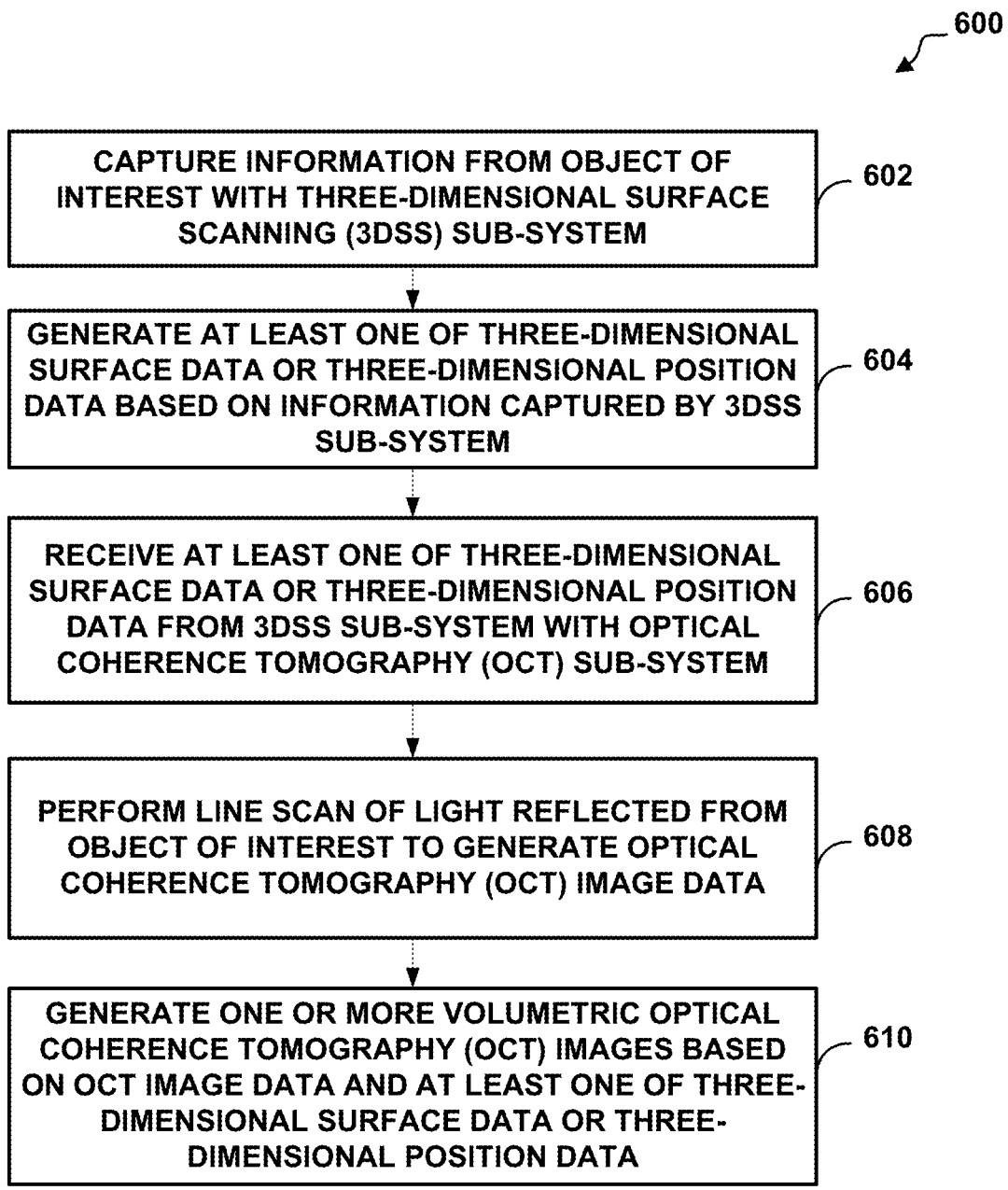
FIG. 6 is a flowchart of a method of imaging an object of interest, in accordance with some embodiments.

FIG. 6 is a flowchart of a method 600 of imaging an object of interest with an imaging system, in accordance with some embodiments. For ease of understanding, the method 600 is described from the perspective of the imaging system 105 of FIG. 1-3, however, the method 600 may also be performed by the imaging systems 405 and 505 of FIGS. 4 and 5, respectively.

In the imaging environment 100, the imaging sensor 205 of the 3DSS sub-system 135 captures information in a channel (for example, the light indicative of the three-dimensional measurement volume 138 in an optical channel) from an object of interest 110 (at block 602). The imaging sensor 205 and the OCT imaging sensor 305 share a common spatial frame of reference. In some embodiments, the OCT imaging sensor 305 of the OCT sub-system 140 also captures the information in the channel (for example, the light indicative of the OCT line measurement 143 in the optical channel) from the object of interest 110.

The electronic processor 200 of the 3DSS sub-system 135 generates at least one of three-dimensional surface data or three-dimensional position data (for example, the three-dimensional surface data, the three-dimensional position data, or a combination thereof as described above) based on the information captured by the imaging sensor 205 (at block 604). For example, the electronic processor 200 of the 3DSS sub-system 135 may perform various accordion fringe interferometer techniques that measure three-dimensional points on an object surface. In particular, the electronic processor 200 may control the light source 136 to project two or more coherent beams of light 137, which create a precision interference fringe pattern visible on the surface of the object of interest 110. The electronic processor 200 acquires three or more two-dimensional fringe images by the imaging sensor 205, with the fringe pattern at 0°, +120°, and −120°. The electronic processor 200 may mathematically combine the relative intensities of three or more measurements for each camera pixel of the imaging sensor 205 to calculate a unique distance to the surface of the object of interest 110.

The electronic processor 300 of the OCT sub-system 140 receives the at least one of the three-dimensional surface data or the three-dimensional position data from the 3DSS sub-system 135 (at block 606). In some embodiments, the electronic processor 300 of the OCT sub-system 140 may adjust one or more OCT imaging parameters (for example, reference arm path length, OCT light source intensity, or other suitable OCT imaging parameter) based on the at least one of the three-dimensional surface data or the three-dimensional position data received from the 3DSS sub-system 135.

The electronic processor 300 of the OCT sub-system 140 performs a line scan of light reflected from the object of interest 110 (for example, the light indicative of the OCT line measurement 143) to generate optical coherence tomography (OCT) image data based on the light captured by the OCT sub-system 140 (at block 608). The electronic processor 300 of the OCT sub-system 140 generates one or more optical coherence tomography (OCT) images based on the OCT image data and the at least one of the three-dimensional surface data or the three-dimensional position data (at block 610). In some embodiments, the one or more OCT images generated by the OCT sub-system 140 is a volumetric optical coherence tomography (OCT) image.

The electronic processor 300 may store the one or more OCT images in the memory 310. The electronic processor 300 may output the one or more OCT images to an internal or external device via the input/output interface 315. For example, the electronic processor 300 controls the input/output interface 315 to output the one or more OCT images to the 3DSS sub-system 135, the networking hardware 145, or an external display device. The dental technician may view the one or more OCT images on the external display device to review the object of interest 110.

In some embodiments, the electronic processor 300 may receive the 3DSS image data generated by the 3DSS sub-system 135, and generate a three-dimensional surface scanning and optical coherence tomography (3DSS/OCT) image from the OCT image data, the 3DSS image data, and the at least one of the three-dimensional surface data or the three-dimensional position data. The electronic processor 300 may store the 3DSS/OCT image in the memory 310. The electronic processor 300 may output the 3DSS/OCT image to an internal or external device via the input/output interface 315. For example, the electronic processor 300 controls the input/output interface 315 to output the 3DSS/OCT image to the 3DSS sub-system 135, the networking hardware 145, or an external display device. The dental technician may view the 3DSS/OCT image on the external display device to review the object of interest 110.

Additionally, in some embodiments, the electronic processor 300 may receive the one or more 3DSS images from the 3DSS sub-system 135 and store the one or more 3DSS images in the memory 310. The electronic processor 300 may output the one or more 3DSS images to an internal or external device via the input/output interface 315. For example, the electronic processor 300 controls the input/output interface 315 to output the one or more 3DSS images to the networking hardware 145 or an external display device. The dental technician may view the one or more 3DSS images on the external display device to review the object of interest 110.

In some embodiments, the electronic processor 200 of the 3DSS sub-system 135 may also generate three-dimensional surface scanning sub-system (3DSS) image data based on the light captured by the imaging sensor 205. In these embodiments, the electronic processor 200 of the 3DSS sub-system 135 may also generate one or more three-dimensional surface scanning (3DSS) images (for example, surface scan images) based on the 3DSS image data. The electronic processor 200 may store the one or more 3DSS images in the memory 210. The electronic processor 200 may output the one or more 3DSS images to an internal or external device via the input/output interface 215. For example, the electronic processor 200 controls the input/output interface 215 to output the one or more 3DSS images to the OCT sub-system 140, the networking hardware 145, or an external display device. A dental technician may view the one or more 3DSS images on the external display device to review the object of interest 110.

Additionally, in some embodiments, the electronic processor 200 may receive the one or more OCT images from the OCT sub-system 140 and store the one or more OCT images in the memory 210. The electronic processor 200 may output the one or more OCT images to an internal or external device via the input/output interface 215. For example, the electronic processor 200 controls the input/output interface 215 to output the one or more OCT images to the networking hardware 145 or an external display device. The dental technician may view the one or more OCT images on the external display device to review the object of interest 110.

In some embodiments, the electronic processor 300 also determines whether the OCT sub-system is within a measurement range of the object of interest 110 using the at least one of the three-dimensional surface data or the three-dimensional position data. When the electronic processor 300 determines that the OCT sub-system 140 is within the measurement range of the object of interest 110, the electronic processor 300 generates the one or more OCT images using the OCT image data and the at least one of the three-dimensional surface data or the three-dimensional position data.

When the electronic processor 300 determines that the OCT sub-system 140 is not within the measurement range of the object of interest, the electronic processor 300 may adjust one or more OCT imaging parameters associated with the OCT sub-system 140 to adjust a measurement range of the OCT sub-system 140 to be equal to a range of the object of interest 110 relative to the OCT sub-system 140. For example, the electronic processor 300 may adjust a length of a reference arm of the OCT sub-system 140, an intensity of light emitted from the light source 141, or other suitable imaging parameter to adjust the measurement range of the OCT sub-system 140 to be equal to the range of the object of interest relative to the OCT sub-system 140.

When the electronic processor 300 determines that the one or more OCT imaging parameters cannot be adjusted to adjust the measurement range of the OCT sub-system 140 to be equal to the measurement range of the object of interest, the electronic processor 300 controls a notification device to output a user-perceptible indication that the OCT sub-system 140 is not within the measurement range of the object of interest. For example, the electronic processor 300 may control a transducer that outputs an audible noise to a user. Alternatively, in some embodiments, the electronic processor 300 may control a light source that outputs a visible indication to the user. In other embodiments, the electronic processor 300 may control a tactile device that outputs a tactile indication to the user. For example, the electronic processor 300 may control the tactile device to increase or decrease the tactile indication based on the difference between the range of the object of interest 110 and the measurement range of the OCT sub-system 140.

In some embodiments, the electronic processor 200 may receive the OCT image data generated by the OCT sub-system 140, and generate one or more three-dimensional surface scanning and optical coherence tomography (3DSS/OCT) images from the 3DSS image data, the OCT image data, and the at least one of the three-dimensional surface data or the three-dimensional position data. Additionally or alternatively, the electronic processor 200 may receive the 3DSS/OCT image from the OCT sub-system 140 and store the 3DSS/OCT image in the memory 210. The electronic processor 200 may output the 3DSS/OCT image to an internal or external device via the input/output interface 215. For example, the electronic processor 200 controls the input/output interface 215 to output the 3DSS/OCT image to the networking hardware 145 or an external display device. The dental technician may view the 3DSS/OCT image on the external display device to review the object of interest 110.

Various features, advantages, and embodiments are set forth in the following claims.

What is claimed is:
1. An imaging system comprising:
a channel configured to receive information from an object of interest;
a three-dimensional surface scanning (3DSS) sub-system configured to
capture information from the object of interest, and
generate at least one of three-dimensional surface data or three-dimensional position data based on the information captured by the 3DSS sub-system; and
an optical coherence tomography (OCT) sub-system configured to
perform a line scan of light reflected from the object of interest and captured by the OCT sub-system,
generate optical coherence tomography (OCT) image data from the line scan,
receive the at least one of the three-dimensional surface data or the three-dimensional position data from the 3DSS sub-system, and
generate one or more optical coherence tomography (OCT) images using the OCT image data and the at least one of the three-dimensional surface data or the three-dimensional position data, wherein the at least one of the three-dimensional surface data or the three-dimensional position data is indicative of a common spatial frame of reference between the 3DSS sub-system and the OCT sub-system.

2. The imaging system of claim 1, further comprising a housing that encloses the channel, the 3DSS sub-system, and the OCT sub-system.

3. The imaging system of claim 1, wherein the 3DSS sub-system is configured to provide the at least one of the three-dimensional surface data or the three-dimensional position data at the same time that the OCT sub-system is configured to perform the line scan.

4. The imaging system of claim 1, wherein the OCT sub-system is further configured to
determine whether the OCT sub-system is within a measurement range of the object of interest based on the at least one of the three-dimensional surface data or the three-dimensional position data, and
generate the one or more OCT images using the OCT image data and the at least one of the three-dimensional surface data or the three-dimensional position data when the OCT sub-system is within the measurement range of the object of interest.

5. The imaging system of claim 1, wherein the OCT sub-system is further configured to
determine whether the OCT sub-system is within a measurement range of the object of interest based on the at least one of the three-dimensional surface data or the three-dimensional position data, and
adjust one or more imaging parameters associated with the OCT sub-system when the OCT sub-system is not within the measurement range of the object of interest.

6. The imaging system of claim 1, wherein the 3DSS sub-system is further configured to
determine whether the OCT sub-system is within a measurement range of the object of interest based on the at least one of the three-dimensional surface data or the three-dimensional position data, and
control the OCT sub-system to generate the one or more OCT images using the OCT image data and the at least one of the three-dimensional surface data or the three-dimensional position data when the OCT sub-system is within the measurement range of the object of interest.

7. The imaging system of claim 1, wherein the 3DSS sub-system is further configured to
determine whether the OCT sub-system is within a measurement range of the object of interest based on the at least one of the three-dimensional surface data or the three-dimensional position data, and
adjust one or more imaging parameters associated with the OCT sub-system when the OCT sub-system is not within the measurement range of the object of interest.

8. The imaging system of claim 1, wherein the 3DSS sub-system includes
a memory;

a light source configured to emit light on the object of interest;

a three-dimensional surface scanning (3DSS) imaging sensor configured to capture the light reflected from the object of interest as the information captured from the object of interest; and an electronic processor electrically connected to the memory and the 3DSS imaging sensor, the electronic processor configured to control the light source to emit the light on the object of interest, and generate the at least one of the three-dimensional surface data or the three-dimensional position data based on the light captured by the 3DSS imaging sensor.

9. The imaging system of claim 1, wherein the OCT sub-system includes a memory;

a light source configured to emit light on the object of interest;

an optical coherence tomography (OCT) imaging sensor configured to capture the light reflected from the object of interest; and an electronic processor electrically connected to the memory and the OCT imaging sensor, the electronic processor configured to control the light source to emit the light on the object of interest, perform the line scan of the light captured by the OCT imaging sensor, generate the OCT image data from the line scan, receive the at least one of the three-dimensional surface data or the three-dimensional position data from the 3DSS sub-system, and generate the one or more OCT images using the OCT image data and the at least one of the three-dimensional surface data or the three-dimensional position data.

10. The imaging system of claim 1, wherein the 3DSS sub-system is further configured to:

generate three-dimensional surface scanning sub-system (3DSS) image data from the information captured by the 3DSS imaging sensor, and generate one or more three-dimensional surface scanning (3DSS) images from the 3DSS image data.

11. The imaging system of claim 10, wherein the OCT sub-system is further configured to receive the 3DSS image data from the 3DSS sub-system, and generate one or more three-dimensional surface scan and optical coherence tomography (3DSS/OCT) images based on the OCT image data, the 3DSS image data, and the at least one of the three-dimensional surface data or the three-dimensional position data.

12. The imaging system of claim 1, wherein the OCT image data is a volumetric optical coherence tomography (OCT) image data.

13. The imaging system of claim 1, wherein the object of interest is a tooth and surrounding tissue.

14. A method of imaging an object of interest, the method comprising:

capturing, with a three-dimensional surface scanning (3DSS) sub-system, information in a channel from the object of interest;

generating, with the 3DSS sub-system, at least one of three-dimensional surface data or three-dimensional position data based on the information captured by the 3DSS sub-system;

receiving, with an optical coherence tomography (OCT) sub-system, the at least one of the three-dimensional surface data or the three-dimensional position data from the 3DSS sub-system;

performing, with the OCT sub-system, a line scan of light reflected from the object of interest to generate OCT image data; and generating, with the OCT sub-system, one or more optical coherence tomography (OCT) images based on the OCT image data and the at least one of the three-dimensional surface data or the three-dimensional position data.

15. The method of claim 14, further comprising:

determining whether the OCT sub-system is within a measurement range of the object of interest using the at least one of three-dimensional surface data or the three-dimensional position data; and responsive to determining that the OCT sub-system is within the measurement range of the object of interest, generating, with the OCT sub-system, the one or more OCT images using the OCT image data and the at least one of the three-dimensional surface data or the three-dimensional position data.

16. The method of claim 14, further comprising:

determining whether the OCT sub-system is within a measurement range of the object of interest using the at least one of three-dimensional surface data or the three-dimensional position data; and responsive to determining that the OCT sub-system is not within the measurement range of the object of interest, adjusting, with the OCT sub-system, one or more imaging parameters associated with the OCT sub-system.

17. The method of claim 14, further comprising:

generating, with the 3DSS sub-system, a three-dimensional surface scanning sub-system (3DSS) image data based on the information captured by the 3DSS sub-system;

receiving, with the 3DSS sub-system, the OCT image data from the OCT sub-system; and generating, with the 3DSS sub-system, one or more three-dimensional surface scan and optical coherence tomography (3DSS/OCT) images from the OCT image data, the 3DSS image data, and the at least one of the three-dimensional surface data or the three-dimensional position data.

18. The method of claim 14, further comprising:

generating, with the 3DSS sub-system, a three-dimensional surface scanning sub-system (3DSS) image data based on the information captured by the 3DSS sub-system;

receiving, with the OCT sub-system, the 3DSS image data from the 3DSS sub-system; and generating, with the OCT sub-system, one or more three-dimensional surface scan and optical coherence tomography (3DSS/OCT) images from the OCT image data, the 3DSS image data, and the at least one of the three-dimensional surface data or the three-dimensional position data.

19. The method of claim 14, wherein the OCT image data is a volumetric optical coherence tomography (OCT) image data.

20. The method of claim 14, wherein the object of interest is a tooth and surrounding tissue.

* * * * *